US008657602B2

(12) United States Patent
Han et al.

(10) Patent No.: US 8,657,602 B2
(45) Date of Patent: Feb. 25, 2014

(54) WAVED IMPLANT INTEGRATING SOFT TISSUE AREA AND OSSEOUS TISSUE AREA

(75) Inventors: Chong-Hyun Han, Seoul (KR); Shin koo Kim, Seoul (KR)

(73) Assignee: Warantec, Seoul (KR)

( * ) Notice: Subject to any disclaimer, the term of this patent is extended or adjusted under 35 U.S.C. 154(b) by 335 days.

(21) Appl. No.: 12/485,761

(22) Filed: Jun. 16, 2009

(65) Prior Publication Data

US 2009/0305193 A1 Dec. 10, 2009

Related U.S. Application Data

(63) Continuation-in-part of application No. 11/909,702, filed as application No. PCT/KR2006/001131 on Mar. 28, 2006, now abandoned.

(30) Foreign Application Priority Data

Mar. 28, 2005 (KR) .......................... 10-2005-25585

(51) Int. Cl.
*A61C 8/00* (2006.01)

(52) U.S. Cl.
USPC .......................................................... 433/173

(58) Field of Classification Search
USPC ....................................... 433/172–176, 201.1
See application file for complete search history.

(56) References Cited

U.S. PATENT DOCUMENTS

| 5,364,268 | A * | 11/1994 | Lazzara et al. ................. 433/173 |
| 5,588,838 | A * | 12/1996 | Hansson et al. ............... 433/173 |
| 6,547,564 | B1 * | 4/2003 | Hansson ........................ 433/174 |
| 6,655,961 | B2 * | 12/2003 | Cottrell ......................... 433/173 |
| 6,672,872 | B2 * | 1/2004 | Cottrell ......................... 433/173 |
| 7,112,063 | B2 * | 9/2006 | Bulard et al. ................. 433/174 |
| 2003/0104337 | A1 * | 6/2003 | Cottrell ......................... 433/173 |
| 2003/0104338 | A1 * | 6/2003 | Cottrell ......................... 433/173 |
| 2003/0120279 | A1 * | 6/2003 | Hansson ........................ 606/73 |
| 2004/0006346 | A1 * | 1/2004 | Holmen et al. ................. 606/73 |
| 2004/0142304 | A1 * | 7/2004 | Cottrell ......................... 433/173 |
| 2005/0014108 | A1 * | 1/2005 | Wohrle et al. ................. 433/173 |
| 2005/0100861 | A1 * | 5/2005 | Choi et al. ..................... 433/165 |
| 2005/0214714 | A1 * | 9/2005 | Wohrle .......................... 433/173 |
| 2007/0099153 | A1 * | 5/2007 | Fromovich .................... 433/174 |

FOREIGN PATENT DOCUMENTS

| KR | 10-2005-0101097 | 10/2005 |
| KR | 10-2006-0064348 | 6/2006 |

OTHER PUBLICATIONS

International Preliminary Report on Patentability and Written Opinion of the International Searching Authority, mailed Oct. 3, 2007, for International Application No. PCT/KR2006/001131.

* cited by examiner

*Primary Examiner* — Robyn Doan
*Assistant Examiner* — Matthew Nelson
(74) *Attorney, Agent, or Firm* — Klarquist Sparkman, LLP

(57) ABSTRACT

Disclosed herein is a waved implant integrating a soft tissue area and an osseous tissue area. The implant is connected at an upper end thereof to a process tooth. The implant includes a screw portion, a flange and a soft tissue area. The screw portion is inserted into an alveolar bone. The flange is connected to the upper end of the screw portion and inserted into the alveolar bone. The flange has on the upper end thereof a waved shape that is concave in front and rear portions thereof and is convex in left and right portions thereof. The flange comprises on the circumferential surface thereof a fine threaded portion having a thread pitch and/or a thread height smaller and denser than those of the screw portion. A plurality of waved microthreads is formed on the fine threaded portion. The soft tissue area is combined with the upper end of the flange in a body.

12 Claims, 24 Drawing Sheets

Prior Art

WAVED IMPLANT INTEGRATING SOFT TISSUE AREA AND OSSEOUS TISSUE AREA

CROSS REFERENCE TO RELATED APPLICATIONS

The present application is a continuation-in-part of U.S. application Ser. No. 11/909,702, filed Sep. 25, 2007 now abandoned, which is a U.S. National Stage of International Application No. PCT/KR2006/001131, filed Mar. 28, 2006, which was published in English under PCT Article 21(2), which in turn claims the benefit of Korean Patent Application No. KR 10-2005-25585, filed Mar. 28, 2005.

BACKGROUND OF THE INVENTION

1. Field

The present application relates to a waved implant integrating a soft tissue area and an osseous tissue area and, more particularly, to a waved implant integrating a soft tissue area and an osseous tissue area that prevents fine motion of an artificial tooth, keeps the implanted vicinities clean of infection and preserves the gingival shape of the natural teeth.

2. Description of the Related Art

Generally, one of the functions specific to teeth is grinding food so that it can be digested easily. People who lose their teeth cannot chew food to promote good digestion. Accordingly, such people cannot eat their fill and cannot take in nutrition sufficient for staying in good health.

If a permanent tooth, i.e. a tooth exchanged for a milk tooth in childhood, is lost, a further tooth will not grow and take its place. Accordingly, it is necessary to restore the masticatory function by rehabilitating the lost tooth and its surroundings via a prosthetic dental treatment.

However, general dental treatments may somewhat damage the neighboring teeth, gums and osseous tissues. Even wearing dentures comes with the drawbacks that it decreases the masticatory function and they are a foreign body which causes inconvenience, and the like, compared with the natural teeth.

One of the solutions proposed to compensate for the drawbacks of the general prosthetic treatment is artificial tooth transplantation. Artificial tooth transplantation can almost fully restore the entirety of functions and the appearance of the natural tooth.

As described above, the artificial tooth is gaining in popularity recently as an artificial substitute for the natural tooth.

As depicted in FIGS. 1 and 2, the artificial tooth comprises a fixture (artificial tooth root) 103, an abutment 105 and a process tooth 107. The fixture 103 for supporting the process tooth 107 is anchored to an alveolar bone 109 in the vicinity of the lost tooth, like a tooth root in a natural tooth. The abutment 105 put in the gum couples the fixture 103 and the process tooth 107. The process tooth 107 fixed on the abutment 105 in the mouth is designed to assume the same shape and provide the same function as the natural tooth.

Hereinafter, the process of transplanting an artificial tooth 101 to the space where the tooth was lost from will now be discussed.

The process of transplantation is roughly divided into a surgical operation and prosthetic rehabilitation.

Biocompatibility including a blood test, etc. is checked prior to the operation. The transplantation site is selected for the operation. An oral inspection, radiographic test, etc. are carried out in advance for evaluating the quality and quantity of osseous tissues at the transplantation site.

After a series of tests has been completed, the surgical operation is begun.

First, a primary operation is executed to transplant the fixture 103 corresponding to the tooth root of the natural tooth in the alveolar bone 109 under local anesthesia. Here, a gum 111 is excised to expose the alveolar bone 109. Then, the fixture 103 is inserted into the alveolar bone 109 and the gum 111 is sutured.

After a lapse of 3 to 6 months depending on the osseous tissue, a secondary operation is carried out.

The gum 111 sutured is excised again to put the abutment 105 on the upper end of the fixture 103. A connection screw 115 is inserted through an insertion hole 113 formed in the center of the abutment 105. The connection screw 115 is engaged with an engagement hole 117 formed in the center of the fixture 103, coaxial with the insertion hole 113, to fix the abutment 105 on the upper end of the fixture 103 in the gum 111. Like this, extruding the abutment 105 via the gum 111 in the mouth completes the secondary operation.

Subsequently, prosthetic treatment is performed.

First, a gold cylinder 121 is put coaxially on the upper end of the abutment 105. Here, an upper extrusion 119 of the connection screw 115 is inserted into a lower penetration hole 123 having a shape of a truncated cone in the gold cylinder 121. Then, the process tooth 107 is processed on the upper end of the gold cylinder 121 in a general manner. A gold screw 129 is inserted through a tooth hole 127 penetrating along with the centerline of the process tooth 107. By engaging the gold screw 129 with an engagement hole 125 penetrating the upper end of the extrusion 119 of the connection screw 115, the transplantation of the artificial tooth 101 is completed.

However, when applying the artificial tooth 101, for example, to a front tooth, as depicted in FIG. 3, the portion B other than the alveolar bone A, excised to anchor the implant 103 to the alveolar bone A, does not have a supporter for adhering to, differently from the vicinity C of the fixture 103. Accordingly, the alveolar bone B may be resorbed as time goes by and the gum 111 may be involuted.

The involution of the gum 111 has the following problems:

First, it widens the space between the artificial tooth and the gums or the space between the artificial tooth and the alveolar bone, which shortens the durability of the artificial tooth; and second, it widens the space between the artificial tooth and the gums or the space between the artificial tooth and the alveolar bone, which allows bacteria to infiltrate the space, thus causing an odor in and from the mouth and oral diseases.

SUMMARY

Accordingly, the present invention has been made keeping in mind the above problems occurring in the prior art, and an object of the present invention is to provide a waved implant integrating a soft tissue area and an osseous tissue area which reduces the space between an artificial tooth and an alveolar bone to prevent the resorption of the alveolar bone and the involution of the gums, thus prolonging the durability of the artificial tooth, and preventing the deformation of the gums, mouth odors and oral diseases.

Another object of the present invention is to provide a waved implant integrating a soft tissue area and an osseous tissue area in which the edge of the upper end of the implant has a saddle shape to correspond to an alveolar bone and a gum of a patient, so that the alveolar bone surrounding the implant, in particular, the upper portion of the alveolar bone, can be closely adhered to the upper end of the implant without forming a gap, thus reliably preventing the resorption of the alveolar bone.

A further object of the present invention is to provide a waved implant integrating a soft tissue area and an osseous tissue area in which a plurality of microthreads is formed in the circumferential outer surface of the upper end of the implant within a predetermined width, thus increasing the coherence to the gum and a cortical bone formed above the alveolar bone.

In order to accomplish the above objects, the present invention provides a waved implant integrating a soft tissue area and an osseous tissue area, the implant being connected at an upper end thereof to a process tooth, the implant including: a screw portion inserted into an alveolar bone; a flange connected to an upper end of the screw portion and inserted into the alveolar bone, the flange having on an upper end thereof a waved shape that is concave in front and rear portions thereof and is convex in left and right portions thereof, the flange comprising on a circumferential outer surface thereof a fine threaded portion having a thread pitch and/or a thread height smaller and denser than those of the screw portion, with a plurality of waved microthreads formed on the fine threaded portion; and a soft tissue area combined with an upper end of the flange in a body.

Therefore, in the waved implant according to the present invention, the flange having a waved shape and the soft tissue area are integrally formed with the implant, thus preventing fine motion of the implant, preventing infiltration of bacteria around the implant, and keeping the gum in the shape it was in when holding the natural tooth.

The screw portion may comprise a triangular screw or a rectangular screw, but it is not limited to this.

The surface of the microthreads may be treated to have an average surface roughness in μm units, preferably about 0.5 μm to 2 μm. The surface treatment of the microthreads may be conducted by a blasting, etching or anodizing method, but it is not limited to these.

The waved shape of the flange corresponding to the shape of the upper end of the flange may be formed dually around the circumferential outer surface of the flange having the microthreads.

The shape of the upper end of the soft tissue area may be formed identical with that of the upper end of the flange.

The shape of the upper end of the soft tissue area may be that of a polygon having ears.

The shape of the upper end of the soft tissue area may be even.

The shape of the soft tissue area may be a waveform.

Furthermore, the portion between the soft tissue area and the flange may have a slender shape, referred to as Monroe's waist, which is curved sharply from the flange in an upper and inner direction and extended to the soft tissue area. Here, the angle between the flange and the soft tissue area is about 10° to 90°.

The soft tissue area has the same composition as the osseous tissue area.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Hereinafter, a waved implant integrating a soft tissue area and an osseous tissue area in accordance with the present invention will now be described more fully with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
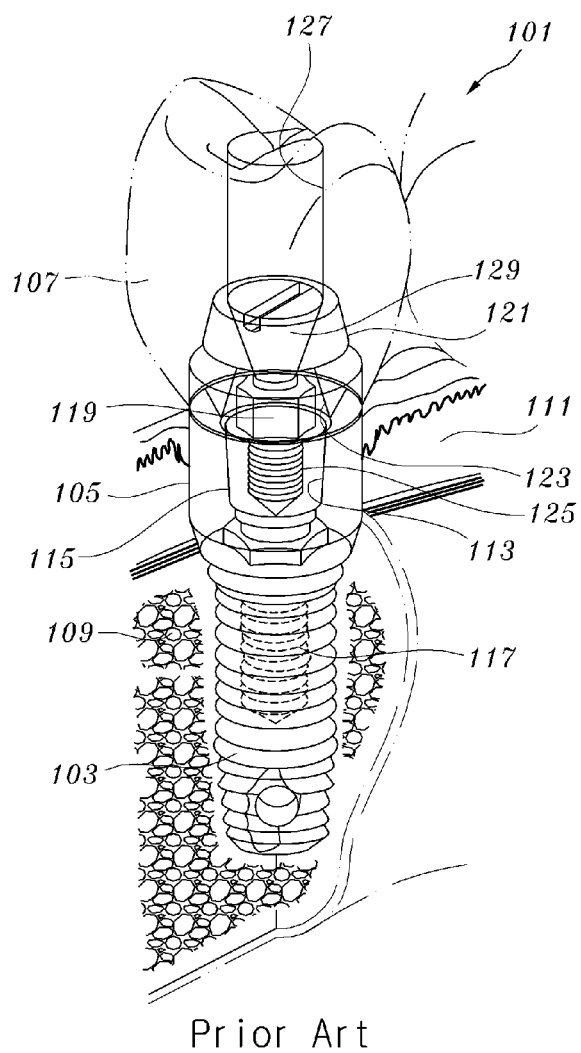
FIG. 1 is a perspective view illustrating a structure of a conventional and typical artificial tooth and a state of the installed artificial tooth.
Figure 2:
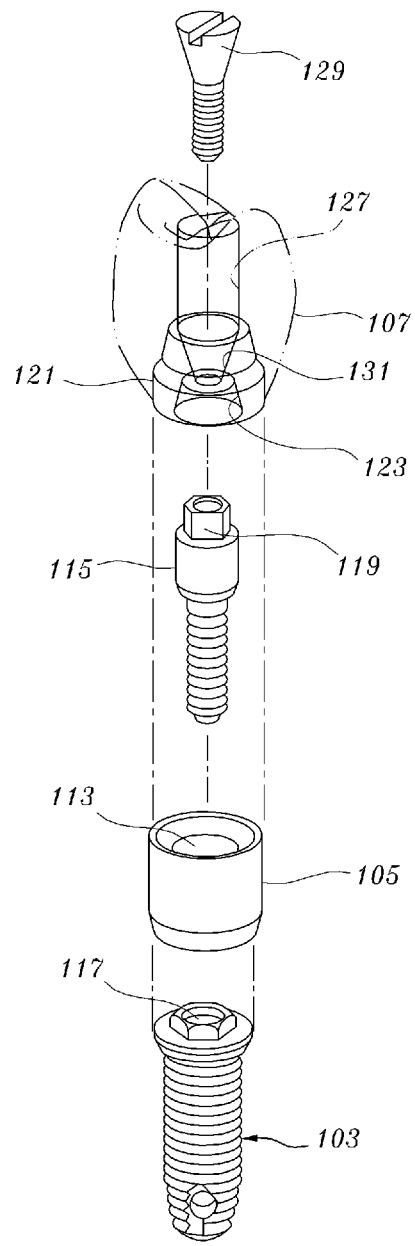
FIG. 2 is an exploded perspective view of FIG. 1.
Figure 3:
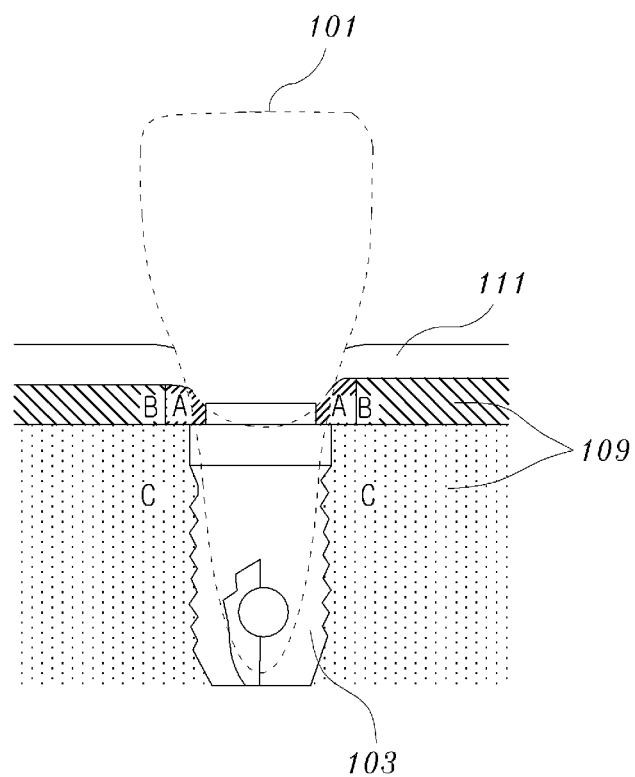
FIG. 3 is a front view showing the conventional artificial tooth transplanted in the site of a front tooth.
Figure 4:
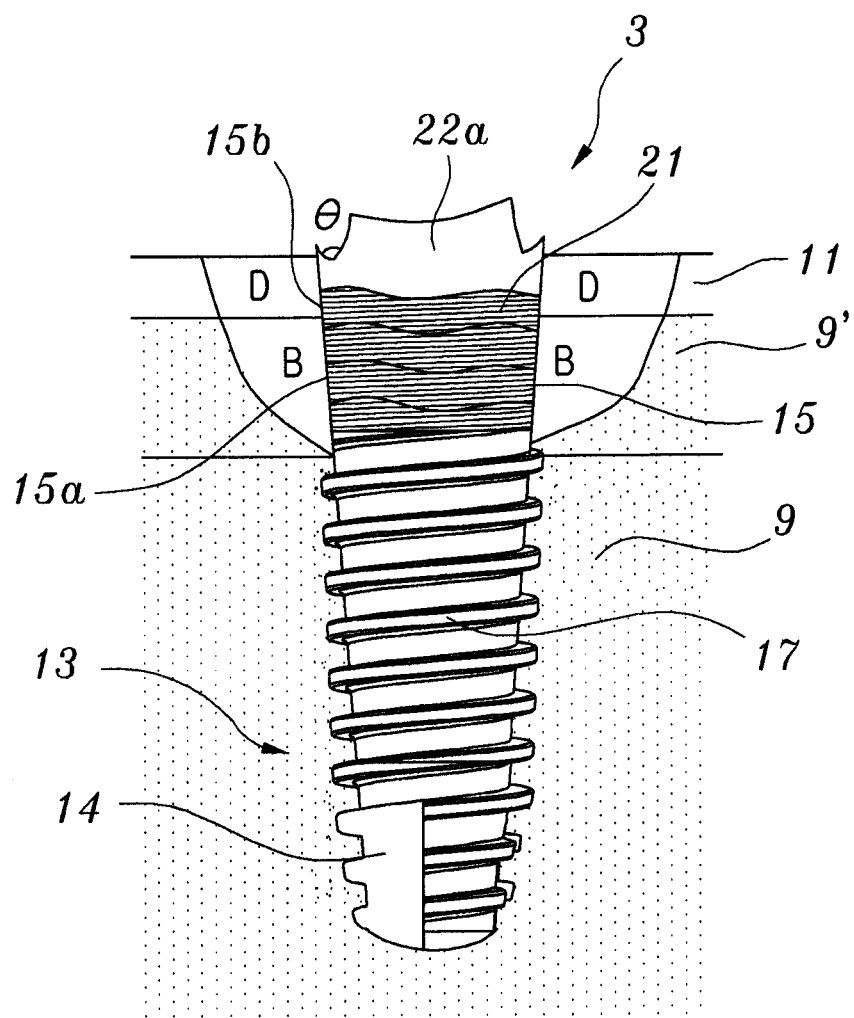
FIG. 4 is a front view depicting the transplantation of a waved implant integrating a soft tissue area and an osseous tissue area in the site of a front tooth, in accordance with an embodiment of the present invention.

FIG. 4 is a front view depicting the transplantation of a waved implant integrating a soft tissue area and an osseous tissue area in the site of a front tooth, in accordance with an embodiment of the present invention. As depicted in FIG. 4, an implant 3 comprises a screw portion 13, a flange 15 connected with the upper end of the screw portion 13 and a soft tissue area 22a integrated with the upper end of the flange 15.

The implant 3 is installed in an alveolar bone 9 by means of the screw portion 13. The screw portion 13 includes a thread 17 and a cutting edge 14.

A triangular screw is generally used, however, a rectangular screw may be used to increase the coherence, which is, however not limited.

In a preferred embodiment of the invention, the upper part of the screw portion 13 has an outer diameter of about 3.0 to 5.0 mm and the lower part of the screw portion 13 has an outer diameter of about 1.0 to 3.0 mm, thus having a shape of a rectilinear body becoming rapidly smaller in the region of the lower part. The thread 17 of the screw portion 13 having a thread depth of about 400 μm, a thread pitch of about 800 μm and an inclined structure at an upward angle of 0° to 10° are formed on the circumferential surface. Accordingly, the implant 3 can be installed in bone tissue by the rotation of the screw portion 13.

The cutting edge 14 is formed by cutting off both ends of the lower part of the screw portion 13 at an angle of about 90 degrees to enhance the installation stability of the implant 3. The cutting edge 14 may increase the bone mineral density in the vicinity of the screw portion 13 since it compresses the vicinity of the screw portion 13 according to the insertion of the implant. At the same time, it is possible to reduce the time required for the bone tissue to adhere to the implant.

In this embodiment, the flange 15 is inserted into the cortical bone 9' on the alveolar bone 9. The upper end of the flange 15 is a curved polygonal shape, such as a trigonal or tetragonal shape, having ears for preventing the involution of the gums. Besides, the upper end of the flange 15 may be formed variously having a wave or sinusoidal wave, a chopping wave or triangular wave, etc. Accordingly, the upper end of the flange 15 may perform a role that prevents the flange 15 of the implant 3 from being resorbed into the alveolar bone, which may happen after the insertion of the implant. For example, if the upper end of the flange 15 is formed in the shape of a waved edge (Taeguk edge), the shape may have a waveform where the front and the rear are concave and the right and the left are convex or a waveform where the front and the rear are convex and the right and left are concave.

Microthreads 21 are densely formed on the body of the flange 15. The microthreads 21 strengthen the coherence with the cortical bone 9' and, at the same time, disperse stress generated during the use of the implant 3. For this purpose, the microthreads 21 having a thread depth and/or a thread pitch smaller than those of the thread 17 of the screw portion 13 are formed densely. For example, the microthreads 21 have a thread depth of about 1 to 25 μm, a thread pitch of about 200 to 400 μm and an upward angle of 0° to 5° and are formed on the circumferential surface of the flange 15.

Figure 7:
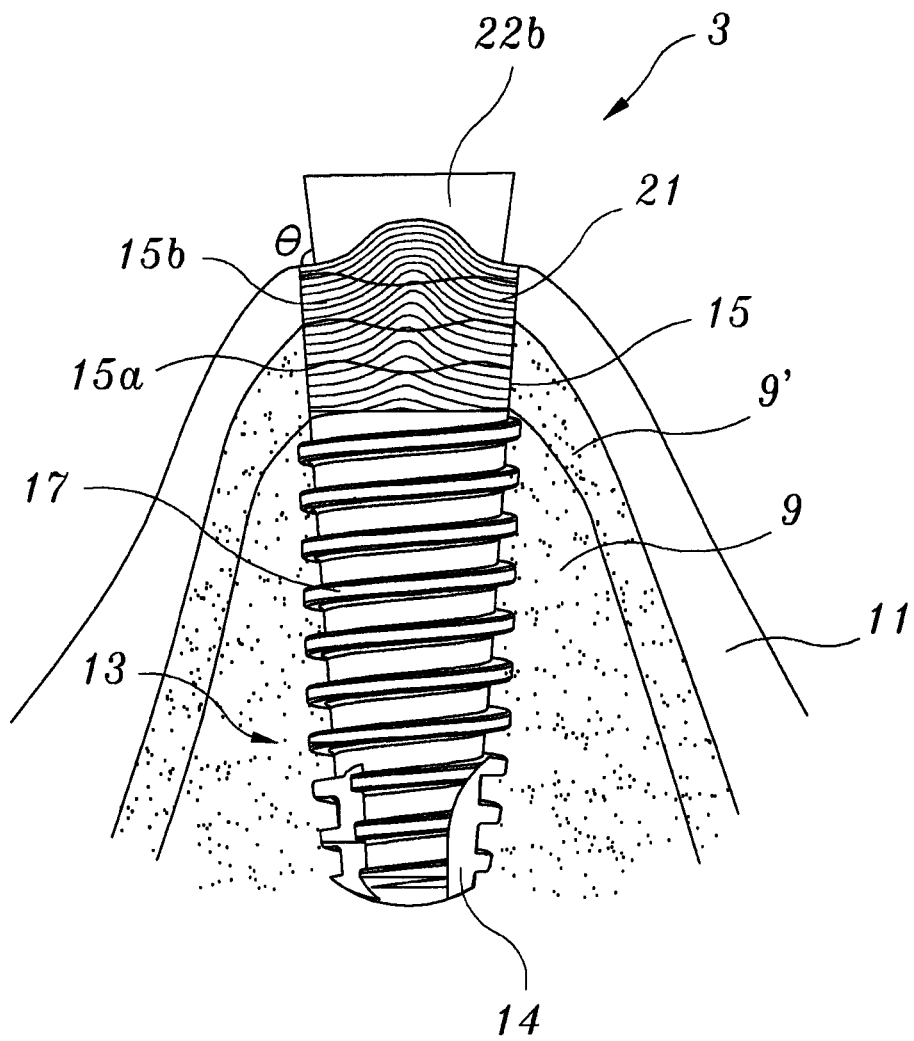

As shown in FIG. 7, in the case where the microthreads 21 have the same shape as the upper end of the flange 15, valley portions of the microthreads 21 are prevented from being exposed to outside of the surface of the upper end of the flange 15. In this case, the surface of the upper end of the flange 15 can be formed to have a smooth shape. Hence, a risk of damaging a gum 11 around front teeth can be reduced, compared to the case where valley portions of the microthreads 21 are exposed to outside of the surface of the upper end of the flange 15.

Here, the microthreads 21 may be formed to have a rectilinear shape inclined at an upward angle of 0° to 5°, or to have the wave edge or the triangular wave like the upper end of the flange 15 over the circumferential surface of the flange.

In particular, it is desirable that the surface of the microthreads 21 be processed roughly to prevent the involution of the gums. The surface treatment of the microthreads 21 may be processed via blasting, etching, anodizing and the like, which is, however, not limited. Examples will be described in detail hereinafter.

The sand blasting method is directed to a surface treatment that reforms the surface of the microthreads 21 roughly by injecting sand or fine sand, such as silica, under high pressure.

Grit blasting method is a surface treatment method that increases the blasting effect on the surface of the microthreads 21 using grits having a sharp edge made by crushing nodular cast iron instead of sand or fine sand.

The etching method corrodes the surface of the microthreads 21 using chemicals to make it rough and uneven.

The surface of the microthreads 21 may be processed by one of the above methods to generate an average surface roughness in the units of μm, preferably, of about 0.5 μm to 2 μm.

Meanwhile, the anodizing method is a surface treatment that anodizes surfaces of aluminum alloy, magnesium alloy, titanium alloy, etc. For example, a metal to be processed is coupled to an anode and an inert metal is connected as a cathode in electrolyte. Then, an electric current is applied to the electrodes to form oxidized films on the surfaces of aluminum, magnesium, titanium, etc. Accordingly, it is possible to increase the corrosion resistance by preventing further oxidizations to the inside of the metal.

In particular, the flange 15 is divided into a contact portion 15a contacting with the cortical bone 9' on the alveolar bone 9 and a contact portion 15b contacting with the gum 11. An end portion B of the cortical bone 9' may adhere well to the contact portion 15a contacting with the cortical bone 9' by means of the microthreads 21 and their rough surface. Besides, the flange 15 may be combined well with the process tooth by means of the microthreads 21 having the waved edge.

In this embodiment, the soft tissue area 22a may be formed in a polygonal shape such as a trigonal, tetragonal, pentagonal, or hexagonal shape, having ears connected with the flange in a body. The ears of the soft tissue area 22a extend to the upper end of the gum 11. Accordingly, the end portion B of the cortical bone 9' that is a portion remaining after excision, is not resorbed. Besides, a top end portion D of the gum 11 does not involute. Furthermore, since the gum does not involute, it is possible to prevent bacteria from infiltrating between the artificial tooth and the gum 11 or between the artificial tooth and the alveolar bone 9, and to keep the form of the gum of the natural tooth.

Here, the top end portion D of the gum 11 may make contact with the contact portion 15b which makes contact with the gum 11 and the soft tissue area 22a at the same time.

Moreover, since the soft tissue 22a is extended to the upper end of the gum 11 in a body, the installation operation of a process tooth, not depicted, may be readily performed. That is, because the process tooth is installed on the soft tissue area 22a having the integrated structure, the artificial tooth can be seated without fine motion and prevent the gums from involuting additionally to keep the shape of the gum 11 of the natural teeth, thus increasing the aesthetics of it.

The angle between the soft tissue area 22a and the flange 15 may be adjusted to from 10° to 90° depending on the shapes of the process tooth and the soft tissue area 22a. The angle between the soft tissue area 22a and the flange 15 is formed so that the junction between the soft tissue area 22a and the flange 15 can be effectively closed. Accordingly, it is possible to enhance the stability of soft tissue and, at the same time, to prolong the durability or lifetime of the artificial tooth.

Besides, the composition of the soft tissue area 22a is identical with that of the osseous tissue area; however, the surface of the soft tissue area 22a may be even so that the surface treatment is not done, after a turning. Here, the composition of the soft tissue area 22a includes hydroxyapatite, etc., which is, however, not limited thereto.

Figure 5:
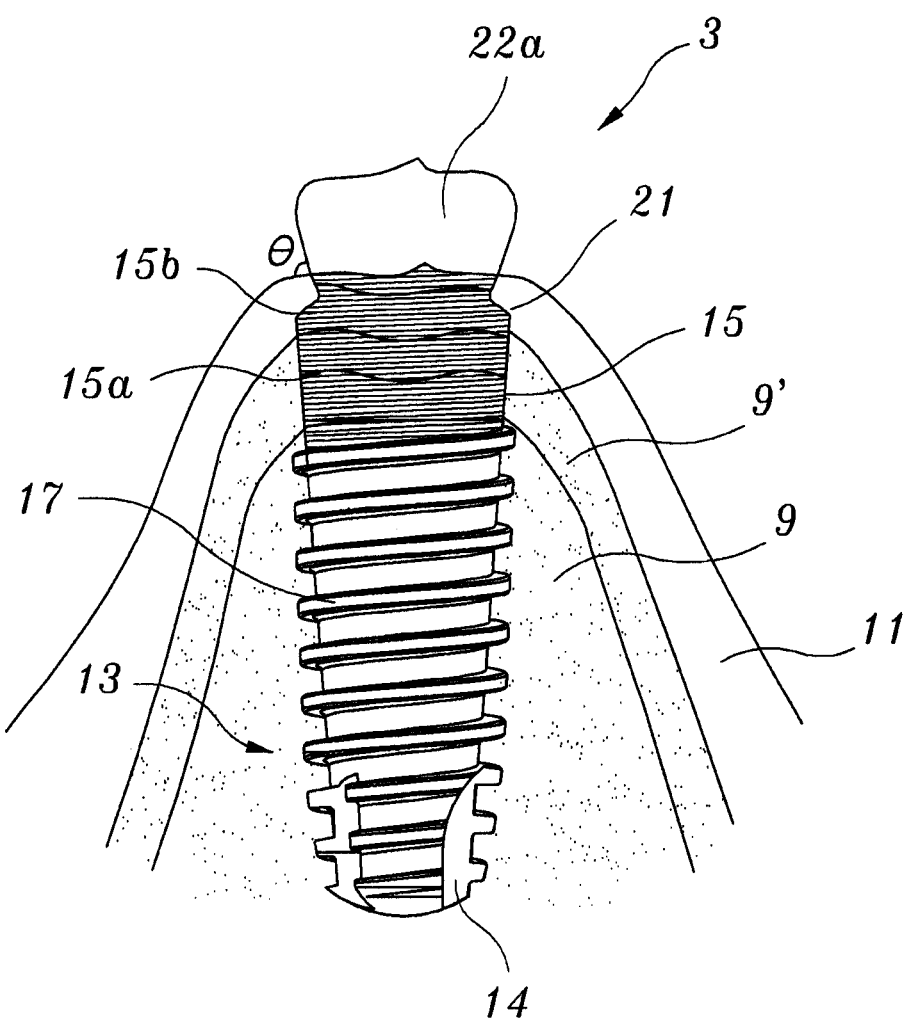
FIG. 5 is a side view of FIG. 4.

FIG. 5 is a side view of FIG. 4. As depicted in FIG. 5, the upper end of the flange 15 is formed of a polygonal shape having a vertex and the soft tissue area 22a has the same shape as the flange 15, thus preventing the fine motion of the implant 3.

Since the soft tissue area 22a is integrally formed with the implant 3 and the flange 15 having the waved shape is extended to the gum 11, it is possible to prevent the resorption of the cortical bone 9' and the involution of the gum 11 due to the excision, thus preventing the infiltration of bacteria.

Furthermore, the portion between the soft tissue area 22a and the flange 15 may have a slender shape, referred to as Monroe's waist, which is curved sharply from the flange 15 in an upper and inner direction and extended to the soft tissue area 22a. Thereby, it is possible to increasingly prevent the involution of the gum 11.

Figure 6:
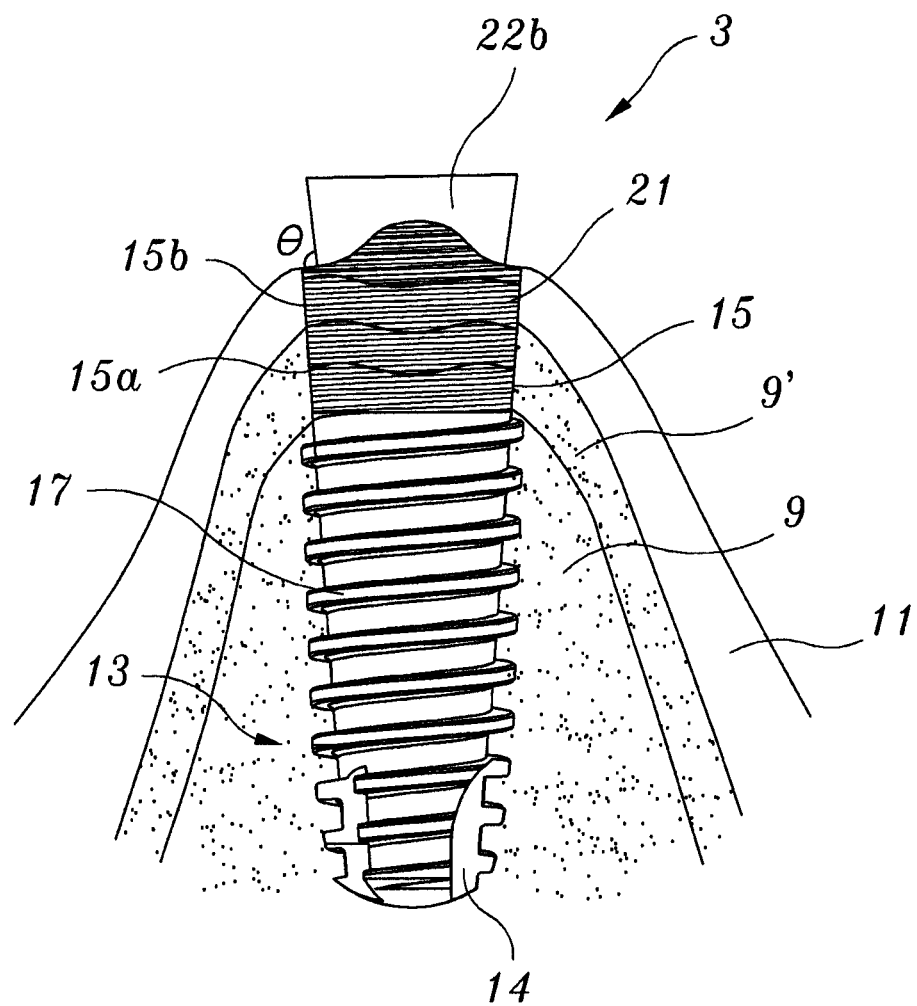
FIGS. 6 through 8 are side views depicting the transplantation of a waved implant integrating a soft tissue area and an osseous tissue area in the site of a front tooth, in accordance with another embodiment of the present invention.

Meanwhile, FIG. 6 is a side view depicting transplantation of a waved implant integrating a soft tissue area and an osseous tissue area in a front tooth site, in accordance with another embodiment of the present invention. As depicted in FIG. 6, the upper end of the flange 15 has a hemispheric shape and the lower end has a waved shape, thus preventing fine motion of the implant 3. The upper end of the soft tissue area 22b is planar. Since the soft tissue area 22b is integrally formed with the implant 3 and the flange 15 having a hemispheric shape in the middle is extended to the gum 11, it is possible to prevent the resorption of the cortical bone 9' and the involution of the gum 11 due to the excision, thus preventing the infiltration of bacteria.

FIG. 6 shows the microthreads 21 of the flange 15 formed rectilinearly; FIG. 7 depicts the microthreads 21 of the flange 15 formed in a waved shape or sinusoidal shape; and FIG. 8 illustrates the microthreads 21 of the flange 15 formed in a chopping wave or triangular wave.

The other conditions of this embodiment are identical with those described with reference to FIGS. 4 and 5.

Figure 8:
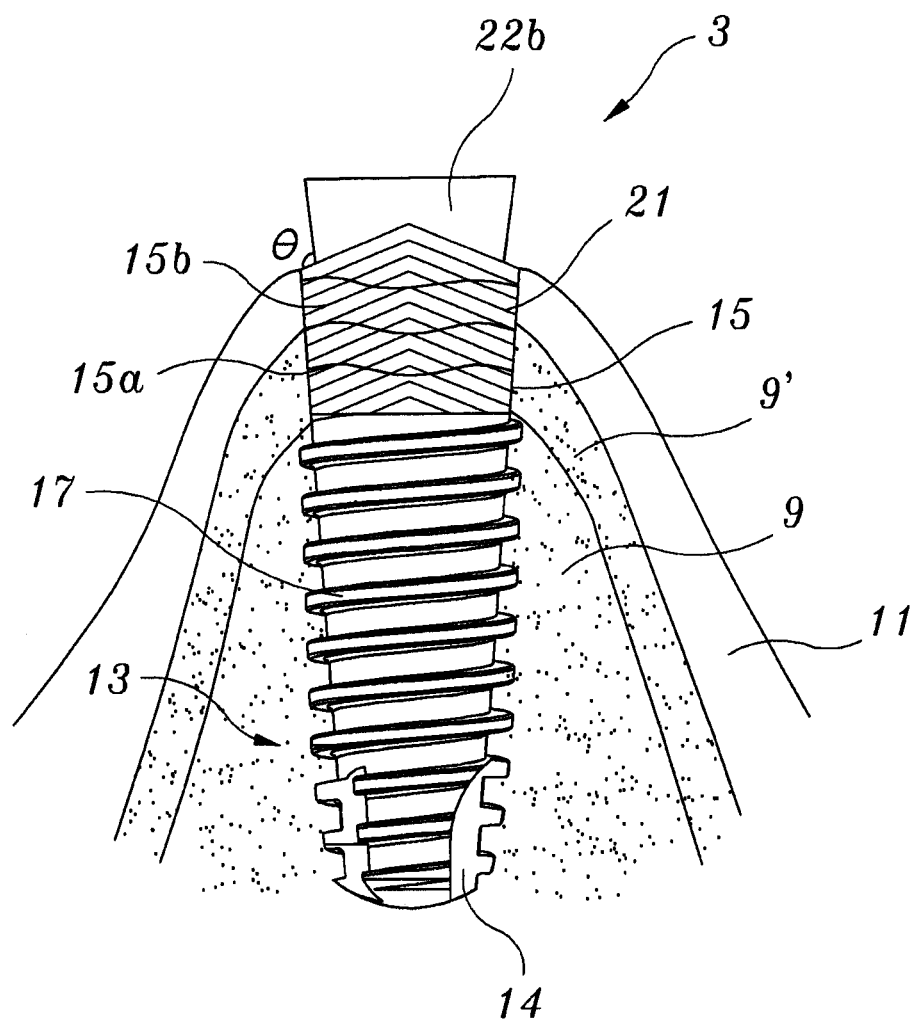
Figure 9:
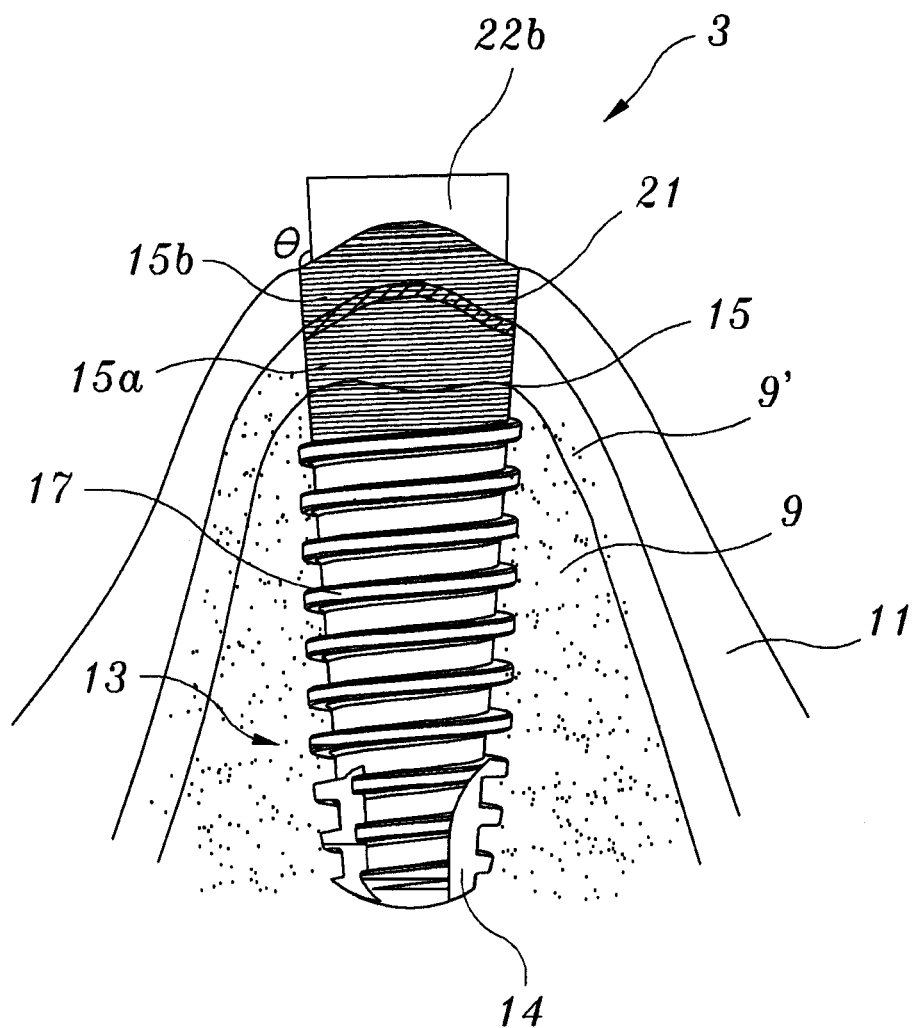
FIGS. 9 through 11 illustrate an implant having a dual waved structure, in accordance with modifications of FIGS. 6 through 8.
Figure 10:
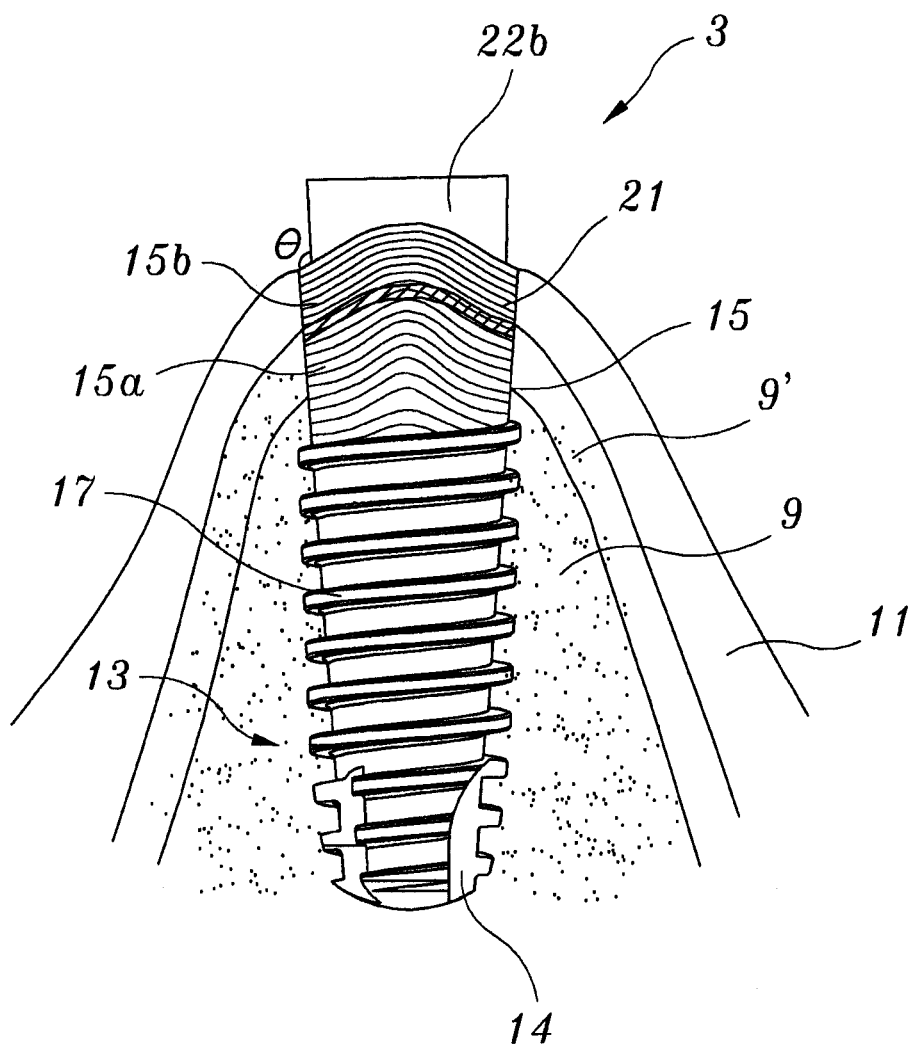
Figure 11:
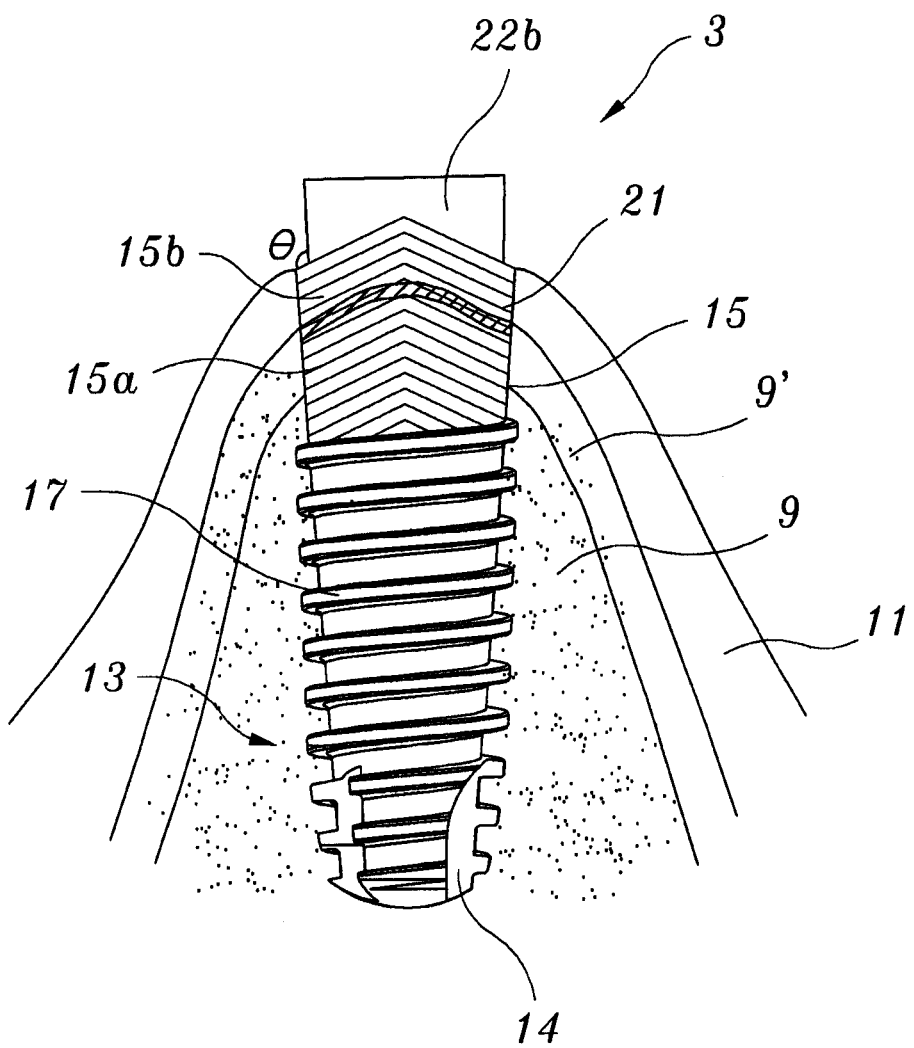

FIGS. 9 through 11 illustrate modifications of FIGS. 6 through 8, wherein a dual wave is formed on the circumferential surface of the flange 15. As shown in FIGS. 9 through 11, the upper end of the flange 15 having the dual wave is formed hemispheric and the lower end of the flange 15 is formed in a dual wave shape, thus further preventing the fine motion of the implant 3. Since the soft tissue area 22b is integrally formed with the implant 3 and the flange 15 having a hemispheric shape in the middle is extended to the gum 11, it is possible to prevent the resorption of the cortical bone 9' and the involution of the gum 11 due to the excision, thus preventing the infiltration of bacteria. The upper end of the soft tissue area 22b has a flat shape.

That is, since the flange 15 has the dual wave shape, it provides resistance to the fine motion of the implant 3, resorption of the cortical bone 9' and the involution of the gum 11 larger than the flange 15 having a single waved shape.

The boundary of the waved shape may be that between the cortical bone contact portion 15a and the gum contact portion 15b or may be an upper or lower portion.

FIG. 9 shows the microthreads 21 of the flange 15 having the dual wave formed rectilinearly; FIG. 10 depicts the microthread 21 of the flange 15 having the dual wave formed in a waved shape or sinusoidal shape; and FIG. 11 illustrates the microthreads 21 of the flange 15 having the dual wave formed in a chopping wave or triangular wave.

The other conditions of these modifications are identical with those described with reference to FIGS. 6 and 8.

Figure 12:
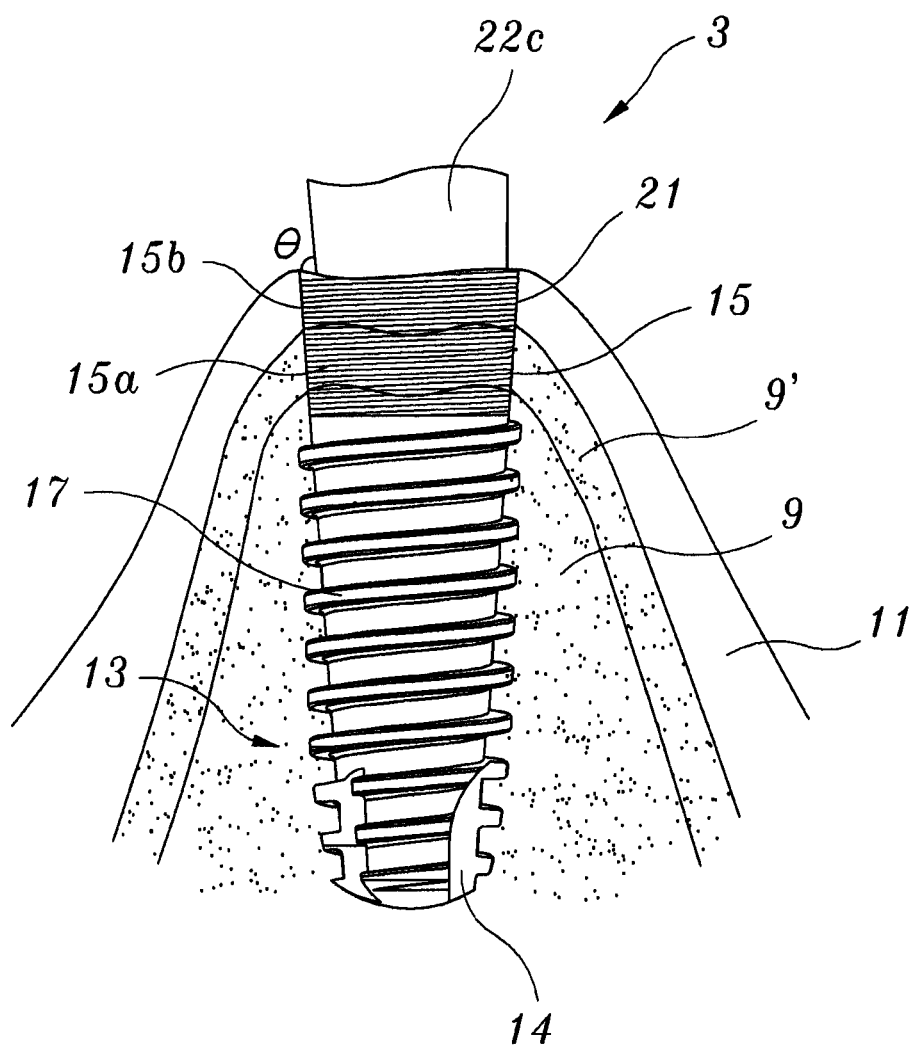
FIG. 12 is a side view showing the transplantation of a waved implant integrating a soft tissue area and an osseous tissue area in the site of a front tooth, in accordance with still another embodiment of the present invention.

FIG. 12 is a side view showing transplantation of a waved implant integrating a soft tissue area and an osseous tissue area in a front tooth site, in accordance with still another embodiment of the present invention. As shown in FIG. 12, since the flange 15 is formed in a waved shape and the soft tissue area 22c is formed in a waved shape as well, it is possible to further prevent the fine motion of the implant 3. Furthermore, because the soft tissue area 22c is integrally formed with the implant 3 and the flange 15 having a waved shape is extended to the gum 11, it is possible to prevent the resorption of the cortical bone 9' and the involution of the gum 11 due to the excision, thus preventing the infiltration of bacteria.

The other conditions of this embodiment are identical with those described with reference to FIGS. 4 and 5.

Figure 13:
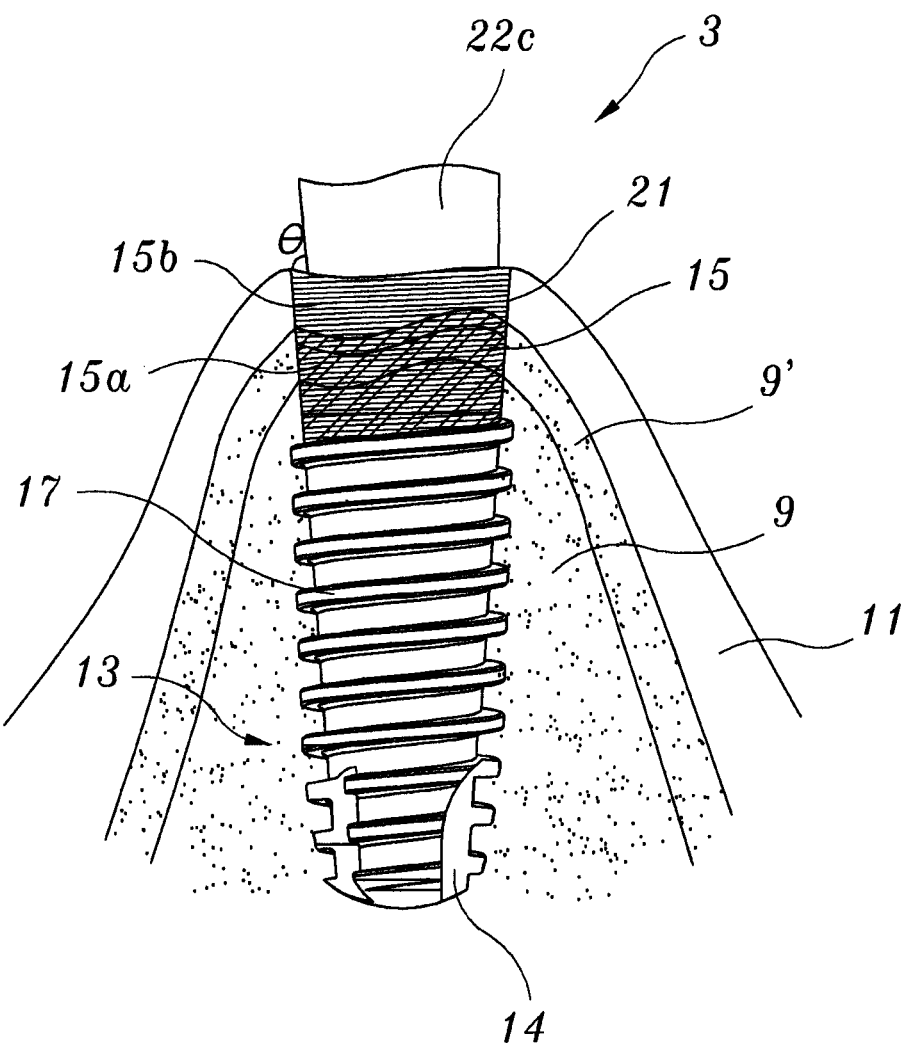
FIG. 13 is a side view illustrating a modification of FIG. 12.
Figure 14:
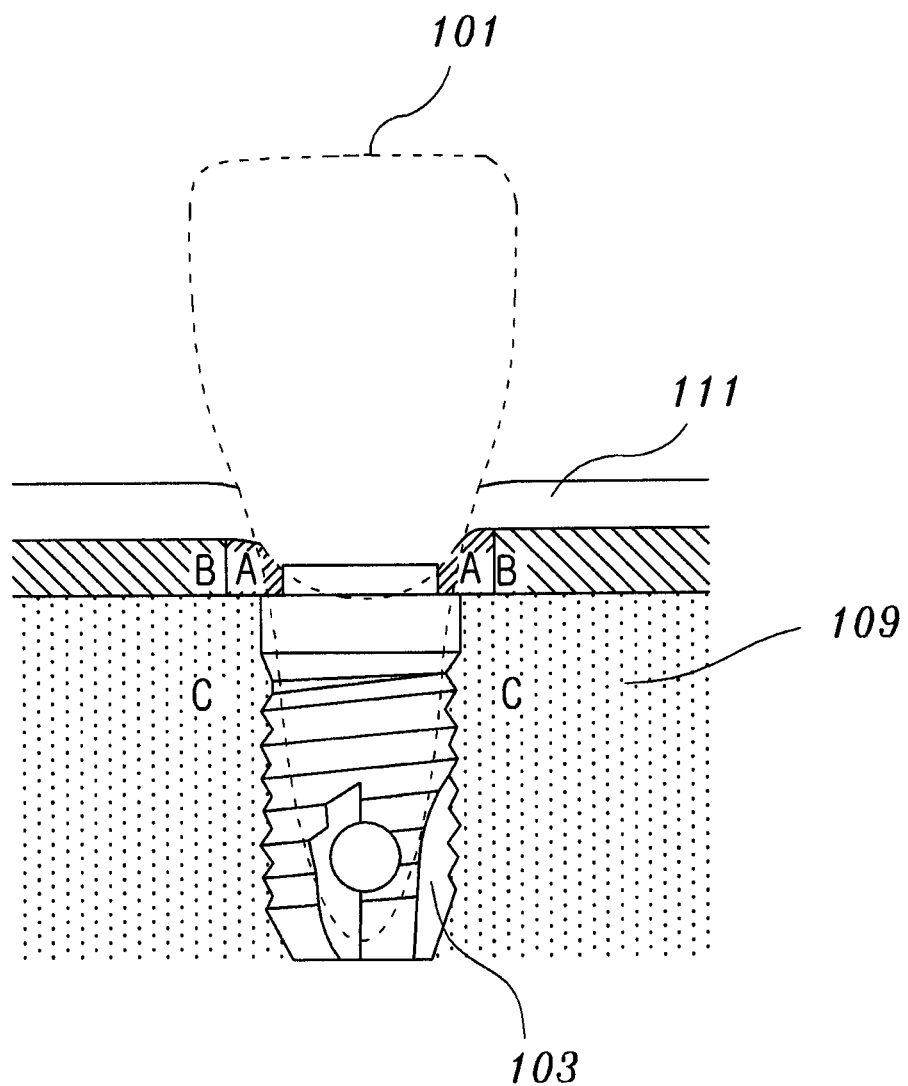
FIG. 14 is a front view showing a screw portion of a conventional artificial tooth transplanted in the site of a front tooth.

FIG. 13 is a side view showing a modification of FIG. 12, wherein a dual wave is formed on the circumferential surface of the flange 15. As shown in FIG. 13, since the flange 15 is formed in a waved shape and the soft tissue area 22c is formed in a waved shape as well, it is possible to further prevent the fine motion of the implant 3. Furthermore, because the soft tissue area 22c is integrally formed with the implant 3 and the flange 15 having a waved shape is extended to the gum 11, it is possible to prevent the resorption of the cortical bone 9' and the involution of the gum 11 due to the excision, thus preventing the infiltration of bacteria.

That is, since the flange 15 has the dual wave shape, it provides resistance to the fine motion of the implant 3, resorption of the cortical bone 9' and the involution of the gum 11 larger than the flange 15 having a single wave shape.

The boundary of the waved shape may be that between the cortical bone contact portion 15a and the gum contact portion 15b or may be an upper or lower portion.

The other conditions of this modification are identical with those described with reference to FIGS. 9 and 11.

Figure 15:
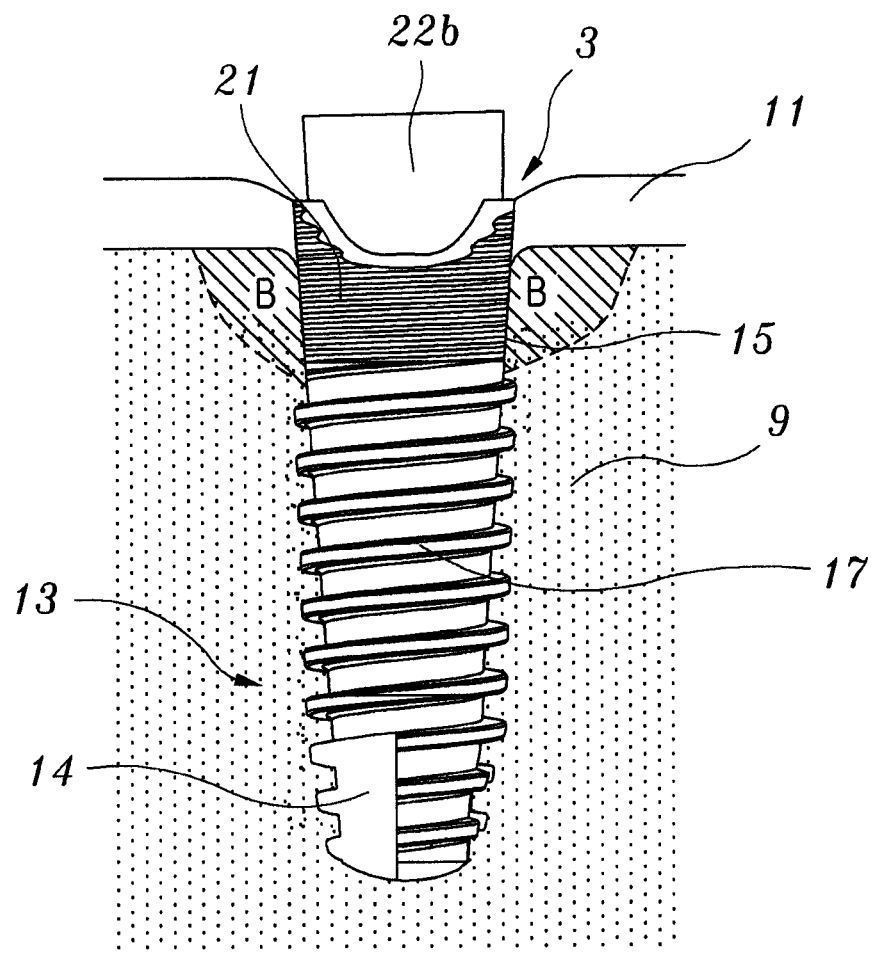
FIG. 15 is a front view showing the transplantation of a waved implant integrating a soft tissue area and an osseous tissue area in a front tooth site, in accordance with still another embodiment of the present invention.
Figure 16:
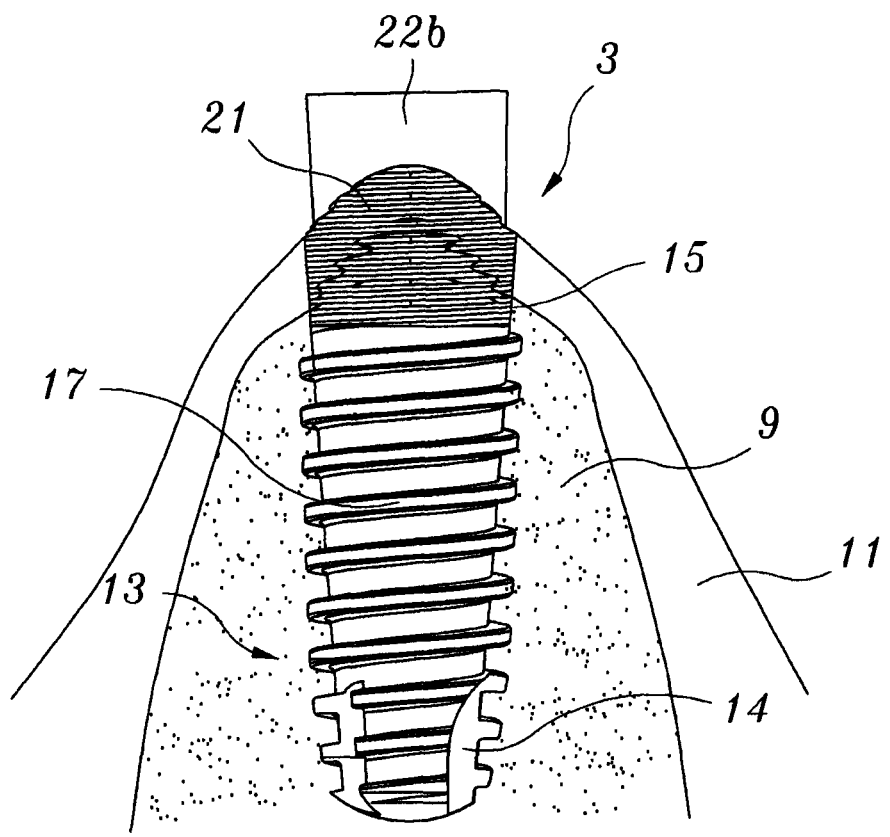
FIG. 16 is a side view of FIG. 15.

Meanwhile, FIGS. 15 and 16 illustrate a waved implant integrating a soft tissue area and an osseous tissue area in a front tooth site, in accordance with still another embodiment of the present invention. As shown in FIGS. 15 and 16, the implant 3 includes a screw portion 13 which is screwed into an alveolar bone 9, and a flange 15 which is coupled to the upper end of the screw portion 13 and is in contact with a gum 11.

Here, the structure of the screw portion 13 is not limited to a special structure, so long as it can be screwed into the alveolar bone 9. Typically, a triangular screw is used for the structure of the screw portion 13, however, a rectangular screw may be used to increase the coherence, as shown in FIG. 15.

In particular, in the waved implant of the present invention, the upper end of the flange 15 generally has a smoothly curved saddle shape wherein the front and the rear are concave and the left and right are convex, such that it corresponds to the contour of the alveolar bone 9 into which the implant 3 is transplanted.

Furthermore, the implant 3 according to this embodiment of the present invention has microthreads 21 which are densely formed on the circumferential outer surface of the upper end of the flange 15 which is in contact with the gum 11 and has a thread pitch of 400 μm, thus enhancing the coherence to the tissue of the gum 11.

Figure 17:
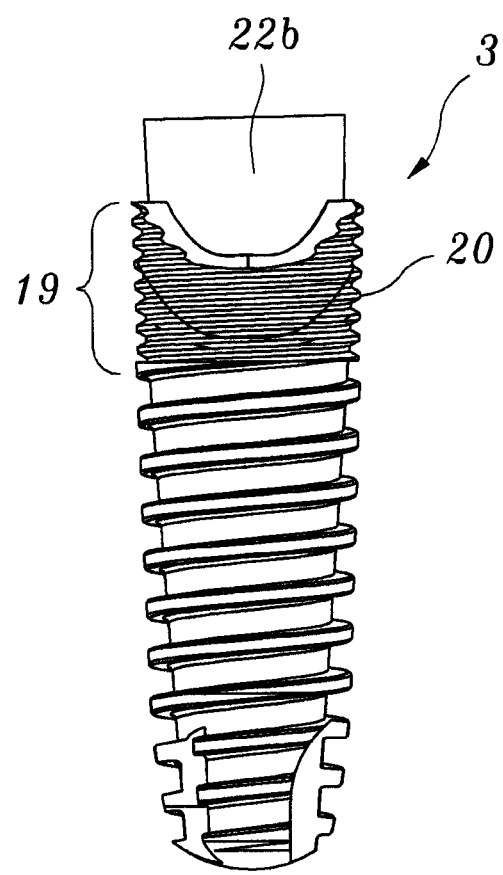
FIG. 17 is a front view illustrating a waved implant integrating a soft tissue area and an osseous tissue area, in accordance with still another embodiment of the present invention.

Moreover, as shown in FIG. 17, a fine threaded portion 19 may be further formed on the circumferential outer surface of the flange 15. A thread formed on the fine threaded portion 19 has a thread pitch and/or thread height less than that of the thread 17 of the screw portion 13, in other words, it is relatively dense. Preferably, the thread of the fine threaded portion 19 comprises a triangular screw to reduce reaction force against the adjacent gum 11 or alveolar bone 9.

Figure 18:
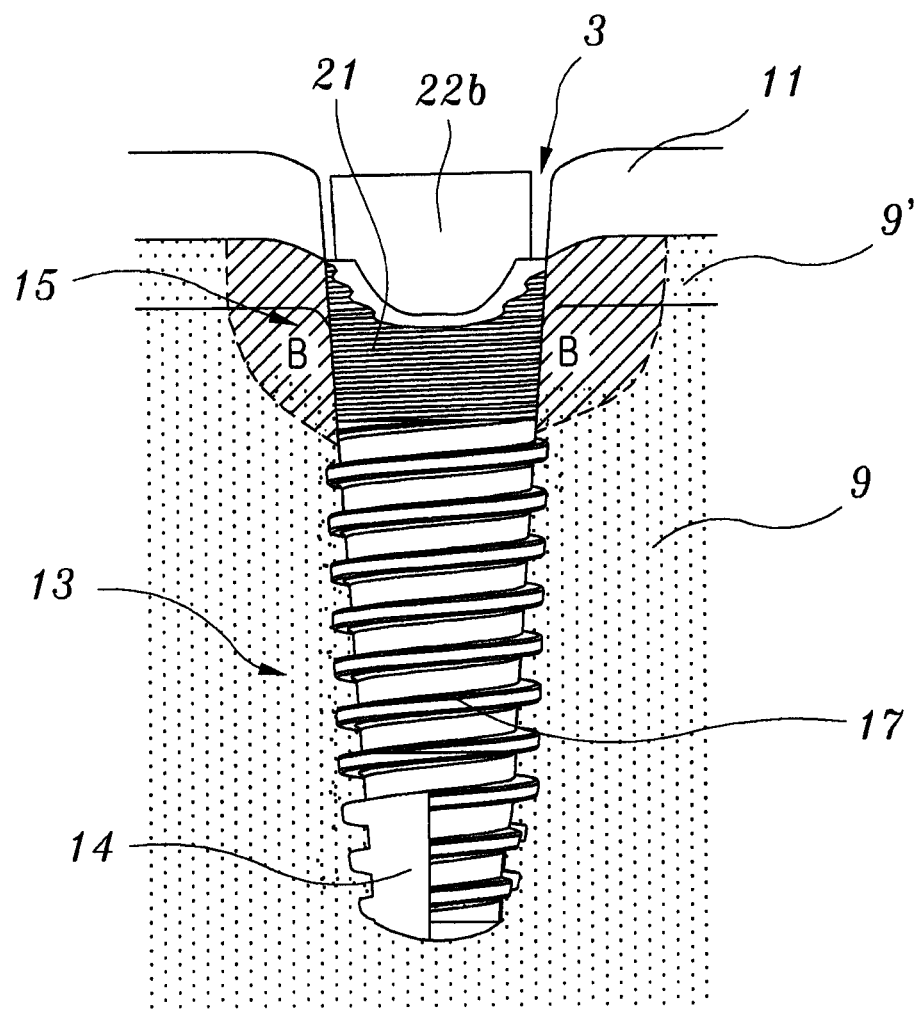
FIG. 18 is a front view showing the transplantation of a waved implant integrating a soft tissue area and an osseous tissue area in a front tooth site, in accordance with still another embodiment of the present invention.

FIG. 18 illustrates a waved implant integrating a soft tissue area and an osseous tissue area in a front tooth site, in accordance with still another embodiment of the present invention. As shown in FIG. 18, in the implant according to this embodiment, the upper end of the flange 15 engages with the cortical bone 9' which is the upper portion of the alveolar bone 9, and microthreads 21 are formed on the circumferential outer surface of the flange 15. Preferably, the flange 15 has on the circumferential outer surface thereof a fine threaded portion 19 which has a pitch and/or a thread height less than that of the thread of the screw portion 13. The fine threaded portion 19 engages with the cortical bone 9' of the alveolar bone 9.

Figure 19:
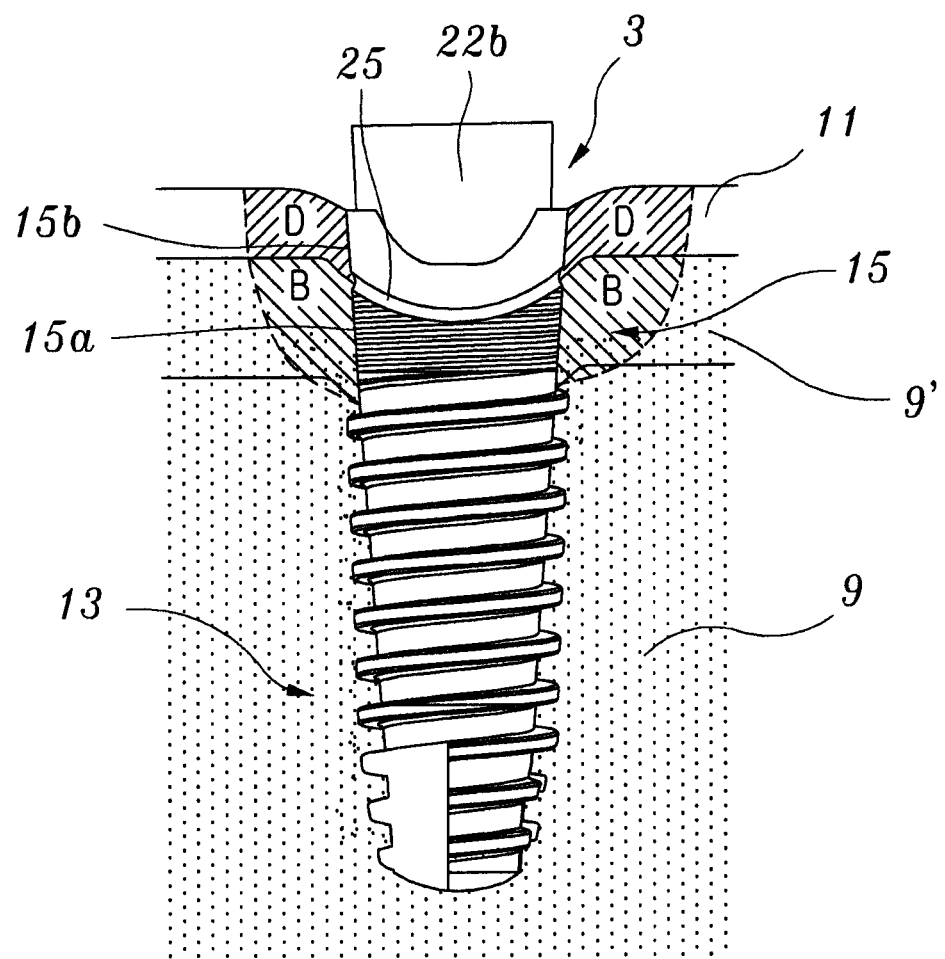
FIG. 19 is a front view showing the transplantation of a waved implant in a front tooth site, in accordance with still another embodiment of the present invention.
Figure 20:
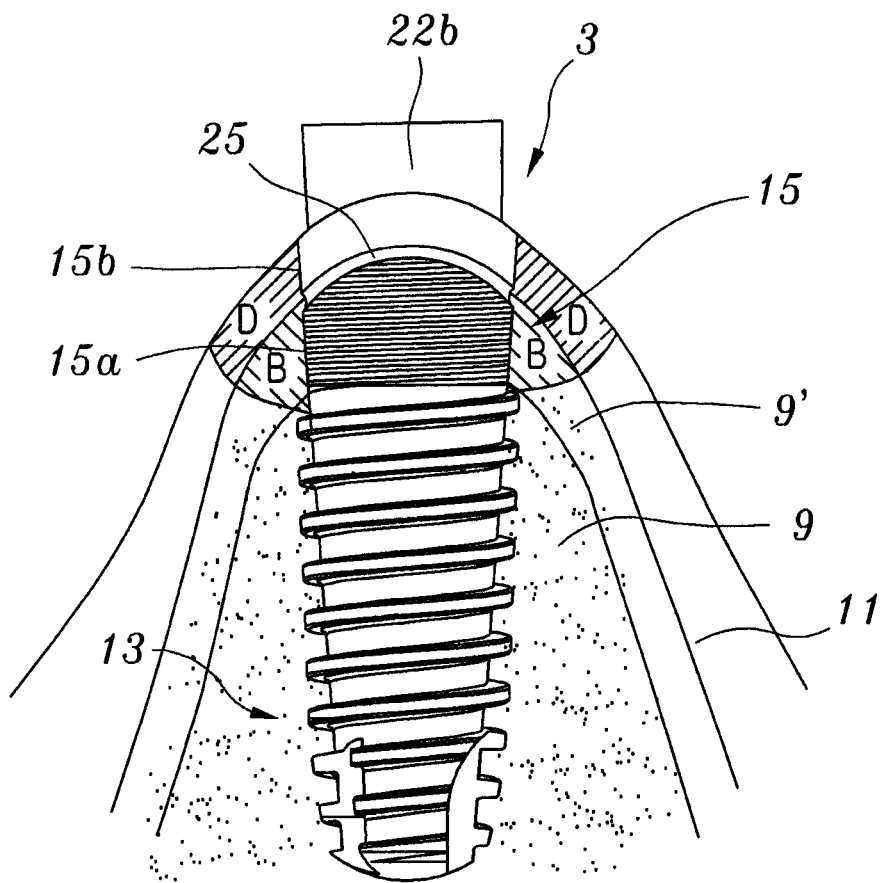
FIG. 20 is a side view showing the transplantation of the waved implant of FIG. 19 in the front tooth site.
Figure 21:
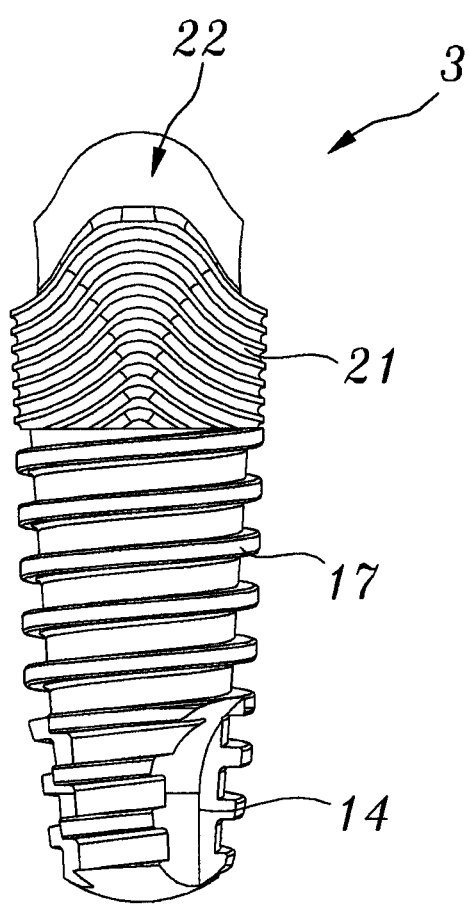
FIG. 21 is a front view showing a waved implant having a soft tissue area, the internal surface of which is tapered in accordance with the present invention.
Figure 22:
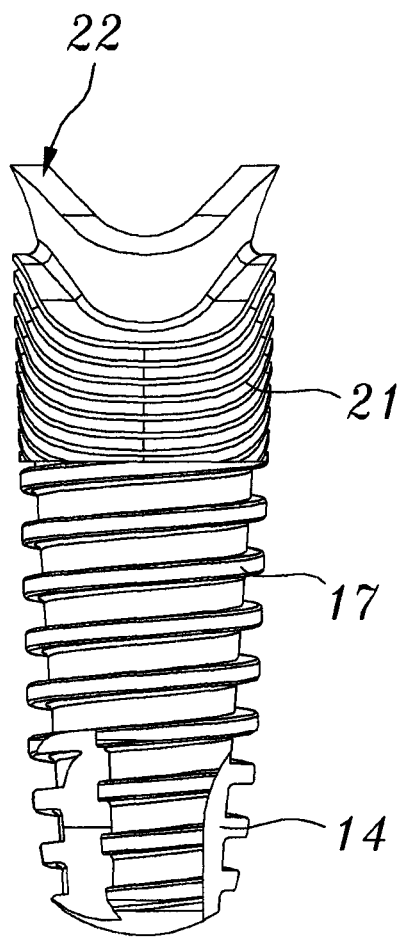
FIG. 22 is a side view showing the waved implant of FIG. 21.
Figure 23:
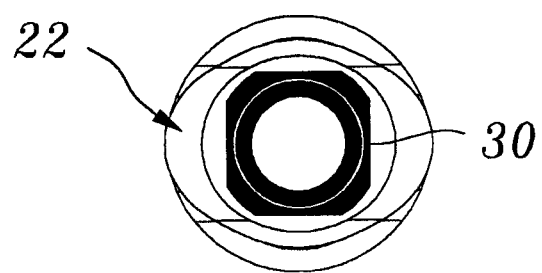
FIG. 23 is a plan view showing the waved implant of FIG. 21.
Figure 24:
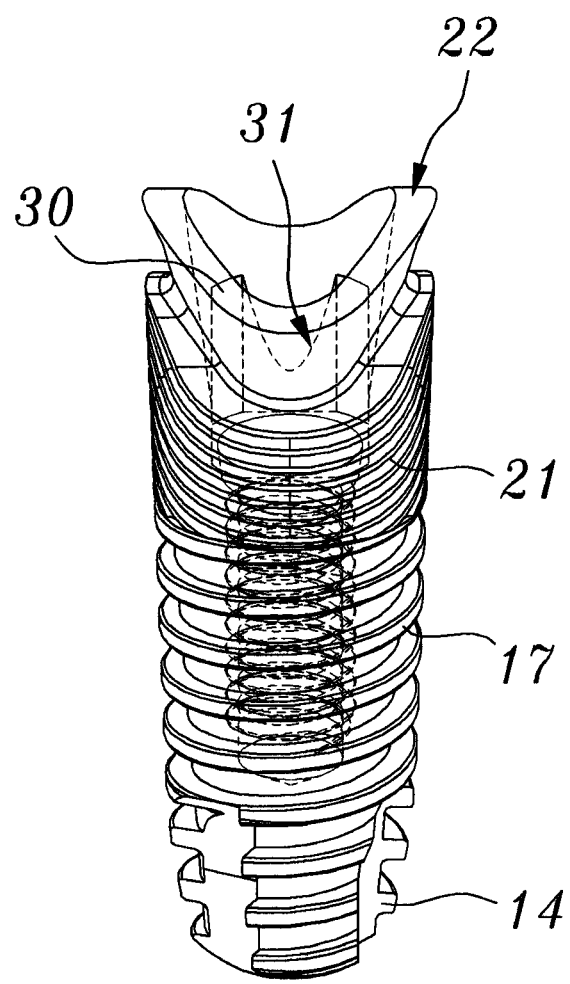
FIG. 24 is a perspective view showing the waved implant of FIG. 21.

FIGS. 19 and 20 illustrate a waved implant integrating a soft tissue area and an osseous tissue area, in accordance with still another embodiment of the present invention. As shown in FIGS. 19 and 20, in this embodiment, an alveolar bone contact portion 15a which engages with the cortical bone 9' of the alveolar bone 9 is formed on the circumferential outer surface of the lower end of the flange 15. A gum contact portion 15b which engages with the gum 11 is formed on the circumferential outer surface of the upper end of the flange 15. The alveolar bone contact portion 15a has microthreads 21 and, preferably, it has a fine threaded portion 19 which has a pitch and/or a thread height less than that of the thread of the screw portion 13. Thus, the alveolar bone contact portion 15a can be reliably adhered to the cortical bone 9' of the alveolar bone 9. The gum contact portion 15b which engages with the gum 11 has an even surface which is not rougher than the microthreads 21 or the fine threaded portion 19, such that it is reliably adhered to the top end portion D of the gum 11. An annular groove 25 is formed in the circumferential outer surface of the junction between the alveolar bone contact portion 15a and the gum contact portion 15b.

The effect of the waved implant integrating the soft tissue area and the osseous tissue area according to the present invention having the above-mentioned structure will be explained below.

The implant 3 of the present invention is screwed into the alveolar bone 9 through the screw portion 13 formed on the circumferential outer surface thereof, in the same manner as that of the general implant of the artificial tooth. The cutting edge 14 which functions to bore the alveolar bone 9 is formed in the lower end of the implant 3. In the embodiments, although a rectangular thread has been illustrated as being used as the thread 17 of the screw portion 13, other kinds of threads, for example, a triangular thread, may be used.

In particular, the implant 3 of the present invention has on the upper end thereof a saddle shape so that the left and the right are convex to correspond to the shape of the adjacent alveolar bone 9 or gum 11. In addition, the front and the rear portions of the upper end of the implant 3 are concave. Thus, the implant 3 can be supported even on the end portion B of the cortical bone 9' of the alveolar bone 9 through the flange 15. Hence, the present invention can prevent the resorption of the end portion B of the cortical bone 9' and the involution of the gum 11 which is disposed above the end portion B.

Furthermore, as shown in FIGS. 17 and 18, the screw portion 13 has a rectangular thread to increase the coherence, with the result that reaction force applied from the screw portion 13 to the adjacent alveolar bone is increased. However, in the present invention, the microthreads 21 may be formed on the circumferential outer surface of the flange 15 which is in contact with the surface layer of the alveolar bone 9 at which the cortical bone 9' is disposed, and, preferably, the fine threaded portion 19 having a triangular thread may be formed thereon. Therefore, the microthreads 21 or the fine threaded portion 19 can be more densely adhered to the cortical bone 9' of the alveolar bone 9 and the reaction force applied from fine grooves or the fine threaded portion 19 can be relatively reduced. As a result, the resorption of the alveolar bone 9 which is adjacent to the flange 15 can be prevented.

As well, as shown in FIGS. 19 and 20, in the case where the gum contact portion 15b is formed on the upper end of the flange 15 in which the front and the rear are concave and the left and the right are convex, the end portion B of the cortical bone 9' of the alveolar bone 9 engages with the alveolar contact portion 15a of the flange 15 on which the microthreads 21 and the fine threaded portion 19 are formed, thus increasing adhesion force between the flange 15 and the alveolar bone 9. Furthermore, the gum contact portion 15b is in contact with the soft tissue area which is the end portion D of the gum 11, thus increasing adhesion force between the gum contact portion 15b and the soft tissue area of the gum 11. Thereby, the present invention can prevent the infiltration of bacteria between the implant 3, the alveolar bone 9 and the gum 11 after the surgically placing the implant, and the resorption of the cortical bone can be prevented. In addition, the implant 3 of the present invention can be reliably adhered to the alveolar bone 9 and the gum 11. Particularly, in the case where the annular groove 25 is formed between the alveolar bone contact portion 15a and the gum contact portion 15b of the flange 15, connective tissue which is the fibroblast of the gum 11 coheres in the annular groove 25, thus increasing the adhesion force between the implant 3 and the soft tissue of the gum 11.

Meanwhile, as shown in FIGS. 21 through 24, the soft tissue area 22 may have a trumpet shape which increases in diameter from the bottom to the top. This can be implemented by tapering the inner and outer surfaces of the soft tissue area 22. As such, in the case where the soft tissue area 22 has a trumpet shape which is increased in diameter from the bottom to the top, a connection screw (not shown) can be easily coupled to the implant 3 after the implant transplantation is completed.

Furthermore, the present invention may be constructed such that a wrench coupling part 30 is provided in the flange 15. In this case, the implant 3 can be easily transplanted into or removed from the gum by fitting the wrench (not shown) into the wrench coupling part 30 and rotating the wrench. The wrench coupling part 30 may be formed through a punching process, which is, however, not limited thereto. In addition, the wrench coupling part 30 may have various shapes, for example, a pentagonal shape, a hexagonal shape, an octagonal shape, etc., and it is not limited to a special shape, so long as the wrench (not shown) can be fitted thereinto.

As such, in the present invention, the cortical bone 9' of the alveolar bone 9 can be satisfactorily formed by the alveolar bone contact portion 15a. The gum contact portion 15b can be reliably adhered to the soft tissue of the gum 11 by cohering of the connective tissue of the gum 11 in the annular groove 25. Therefore, the implant 3 can be reliably adhered to the gum 11 and the alveolar bone 9, and the infiltration of bacteria can be prevented, thus making the transplantation of the implant 3 smooth and reliable.

As described above, since the waved implant integrating the soft tissue area and the osseous tissue area in accordance with the present invention is integrally installed in a bio or artificial soft tissue after a corresponding portion of a gum is excised and sutured, it prevents the resorption of alveolar bone and the involution of the gum, thus preventing the infiltration of bacteria, and maintains the implant clear. Furthermore, it is possible to keep the implant installed for a longer time, which saves time and money, and to increase looks by restoring the gums to their state when the natural tooth was present.

Moreover, in the present invention, the edge of the upper end of the implant has a saddle shape to correspond to the alveolar bone and the gum of the front tooth site. Therefore, the alveolar bone surrounding the implant can closely adhere to the implant without forming a gap therebetween, thus reliably preventing the resorption of the alveolar bone and the involution of the gum. As well, a plurality of fine grooves or a fine threaded portion is formed on the circumferential outer surface of a portion of a flange which is in contact with the cortical bone of the alveolar bone, and a relatively even surface is formed on the circumferential outer surface of a portion of the flange which is in contact with the gum. Thereby, the flange can be reliably adhered to by the cortical bone of the alveolar bone and the gum, thus increasing the coherence to the alveolar bone and the gum surrounding the implant.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of implanting a waved implant integrating a soft tissue area and an osseous tissue area, the implant being adapted to be connected at an upper end thereof to a process tooth, the implant comprising:
   a screw portion adapted to be inserted into an alveolar bone of a patient;
   a flange connected to an upper end of the screw portion and adapted to be inserted into the alveolar bone, the flange having on an upper end thereof a waved shape that is concave in front and rear portions thereof and is convex in left and right portions thereof, the flange comprising on a circumferential outer surface thereof a fine threaded portion having a thread pitch and/or a thread height smaller and denser than those of the screw portion, with a plurality of waved microthreads formed on the fine threaded portion; and
   wherein the soft tissue area is formed as one piece with an upper end portion of the flange, the upper end portion of the flange comprising a hemispheric-shaped portion;
   wherein the osseous tissue area comprises the screw portion and the flange;
   wherein the screw portion comprises a thread and a cutting edge;
   wherein the cutting edge comprises a flat surface portion extending axially along a lower part of the screw portion and intersecting the thread on the lower part of the screw portion,
   wherein the soft tissue area has ears which are connected with the flange in a body and configured to extend to the upper end of the gum when the implant is implanted in the alveolar bone;
   wherein the top end portion of the gum can contact with a contact portion, which makes contact with the gum and the soft tissue area at the same time; and
   wherein the microthreads have a roughened surface formed by a blasting, etching or anodizing surface treatment;
   wherein a portion of the plurality of waved microthreads are formed on the hemispheric-shaped portion, the hemispheric-shaped portion extending above a lowermost end of the soft tissue area;
   the method comprising implanting the screw portion into the alveolar bone of the patient such that the fine threaded portion extends upwardly through the cortical bone and into the gum, the gum surrounds and contacts microthreads on the fine threaded portion, and the hemispheric-shaped portion extends above the top end portion of the gum.

2. The method as set forth in claim 1, wherein the screw portion comprises a triangular screw or a rectangular screw.

3. The method as set forth in claim 1,
   wherein the microthreads of the flange are formed having a structure of a waved shape or a chopping wave shape,
   the microthreads are formed on the circumferential outer surface of the flange and have a thread depth ranging from 1 µm to 25 µm, a thread pitch ranging from 200 µm to 400 µm and an inclined structure at an upward angle of 0° to 5°, and
   the microthreads have an average surface roughness ranging from 0.5 µm to 2 µm.

4. The method as set forth in claim 1, wherein the waved shape of the flange is formed dually.

5. The method as set forth in claim 1,
   wherein the soft tissue area has one of a shape identical with a shape of the flange, a polygonal shape having an ear, a shape which is even in an upper end thereof, and a waved shape.

6. The method as set forth in claim 1, wherein an angle between the flange and the soft tissue area ranges from 10° to 90°.

7. The method as set forth in claim 1, wherein the soft tissue area has the same composition as the osseous tissue area.

8. The method as set forth in claim 1,
   wherein the flange comprises:
   an alveolar bone contact portion adapted to engage with an upper portion of the alveolar bone; and
   a gum contact portion adapted to engage with the gum.

9. The method as set forth in claim 8,
   wherein said plurality of microthreads are formed in circumferential outer surfaces of the alveolar bone contact portion and the gum contact portion.

10. The method as set forth in claim 8,
    wherein an annular groove is formed in a circumferential outer surface of a portion between the alveolar bone contact portion and the gum contact portion.

11. The method as set forth in claim 1,
    wherein the soft tissue area has a trumpet shape which increases in a diameter from a bottom thereof to a top thereof.

12. The method as set forth in claim 1,
    wherein the flange has a wrench coupling part on an upper end of an inner surface thereof.

* * * * *